(12) United States Patent
Wallace et al.

(10) Patent No.: US 6,565,601 B2
(45) Date of Patent: May 20, 2003

(54) METHODS FOR VASCULAR RECONSTRUCTION OF DISEASED ARTERIES

(75) Inventors: George Wallace, Coto De Caza, CA (US); Richard J. Greff, St. Pete Beach, FL (US); Earl H. Slee, Laguna Niguel, CA (US); Thomas J. Whalen, II, Encinitas, CA (US)

(73) Assignee: Micro Therapeutics, Inc., Irvine, CA (US)

( * ) Notice: Subject to any disclaimer, the term of this patent is extended or adjusted under 35 U.S.C. 154(b) by 106 days.

(21) Appl. No.: 09/811,600

(22) Filed: Mar. 20, 2001

(65) Prior Publication Data

US 2002/0169496 A1 Nov. 14, 2002

Related U.S. Application Data

(60) Provisional application No. 60/249,342, filed on Nov. 15, 2000, and provisional application No. 60/252,757, filed on Nov. 21, 2000.

(51) Int. Cl.⁷ .............................. A61F 2/06; A61K 9/08
(52) U.S. Cl. ...................... 623/1.15; 606/108; 523/111
(58) Field of Search ................ 606/108, 200; 523/111; 600/29; 623/1.15

(56) References Cited

U.S. PATENT DOCUMENTS

| | | | |
|---|---|---|---|
| 3,527,224 A | 9/1970 | Rabinowitz et al. | |
| 3,591,676 A | 7/1971 | Hawkins et al. | |
| 4,938,763 A | 7/1990 | Dunn et al. | |
| 5,213,580 A | 5/1993 | Slepian et al. | |
| 5,421,826 A | 6/1995 | Crocker et al. | |
| 5,458,568 A | 10/1995 | Racchini et al. | |
| 5,542,926 A | 8/1996 | Crocker et al. | |
| 5,569,184 A | 10/1996 | Crocker et al. | |
| 5,575,815 A | 11/1996 | Slepian et al. | |
| 5,580,568 A | 12/1996 | Greff et al. | |
| 5,634,946 A | 6/1997 | Slepian et al. | |
| 5,650,447 A | 7/1997 | Keefer et al. | |
| 5,667,767 A | 9/1997 | Greff et al. | |
| 5,674,287 A | 10/1997 | Slepian et al. | |
| 5,695,480 A | 12/1997 | Evans et al. | |
| 5,702,361 A | 12/1997 | Evans et al. | |
| 5,749,915 A | 5/1998 | Slepian et al. | |
| 5,749,922 A | 5/1998 | Slepian et al. | |
| 5,800,538 A | 9/1998 | Slepian et al. | |
| 5,830,178 A | 11/1998 | Jones et al. | |
| 5,843,156 A | 12/1998 | Slepian et al. | |
| 5,855,563 A | 1/1999 | Kaplan et al. | |
| 5,888,546 A | 3/1999 | Ji et al. | |
| 5,894,022 A | 4/1999 | Ji et al. | |
| 5,914,345 A | 6/1999 | Slepin et al. | |
| 5,921,954 A | 7/1999 | Mohr et al. | |
| 5,947,977 A | 9/1999 | Slepian et al. | |
| RE36,370 E | 11/1999 | Li | |
| 5,980,554 A | * 11/1999 | Lenker et al. | ............... 606/108 |
| 6,007,573 A | 12/1999 | Wallace et al. | |
| 6,007,833 A | 12/1999 | Chudzik et al. | |
| 6,017,977 A | 1/2000 | Evans et al. | |
| 6,096,021 A | 8/2000 | Helm et al. | |
| 6,241,719 B1 | 6/2001 | Wallace et al. | |
| 6,248,058 B1 | * 6/2001 | Silverman et al. | ............. 600/29 |
| 6,299,619 B1 | * 10/2001 | Green, Jr. et al. | ........... 606/108 |
| 6,335,384 B1 | * 1/2002 | Evans et al. | ................. 523/113 |
| 6,435,189 B1 | * 8/2002 | Lewis et al. | ................. 128/898 |
| 6,464,724 B1 | * 10/2002 | Lynch et al. | ................. 623/4.1 |
| RE37,950 E | * 12/2002 | Dunn et al. | ................. 523/113 |
| 6,497,722 B1 | * 12/2002 | Von Oepen et al. | ....... 623/1.13 |

OTHER PUBLICATIONS

Aletich, et al., "The Remodeling Technique of Balloon–Assisted Guglielmi Detachable Coil Placement in Wide–Necked Anuerysms: Experience at the University of Illinois at Chicago", *J. Neurosurg*, 93: 388–396 (2000).

(List continued on next page.)

*Primary Examiner*—David H. Willse
*Assistant Examiner*—Suzette J. Jackson
(74) *Attorney, Agent, or Firm*—Burns, Doane, Swecker & Mathis L.L.P.

(57) ABSTRACT

Disclosed are methods for vascular reconstruction of diseased, non-aneurysmal arteries.

9 Claims, 6 Drawing Sheets

OTHER PUBLICATIONS

"Cancer, Principles & Practice of Oncology", 4th Ed., vol. 1, "Cancer Treatment", pp. 545–548 (1993).

Castaneda–Zuniga, et al., *Interventional Radiology*, in Vascular Embolotherapy, Part 1, 1:9–32, Williams & Wilkins, Publishers (1992).

Cognard, et al., "Treatment of Distal Aneurysms of the Cerebellar Arteries by Intraaneurysmal Injection of Glue", *Am J. Neuroradiol.*, 20: 780–784 (1999).

Fischell, et al., "The Beta–Particle–Emitting Radioisotope Stent (Isostent): Animal Studies and Planned Clinical Trials", *Am. J. Cardiol.*, 78(suppl 3A): 45–50 (1996).

Fischell, et al., "Low–Dose, β–Particle Emission From "Stent" Wire Results in Complete, Localized Inhibition of Smooth Muscle Cell Proliferation", *Circulation*, 90(6): 2956–2963 (1994).

Hill–West, et al., "Inhibition of Thrombosis and Intimal Thickening by in situ Photopolymerization of Thin Hydrogel Barriers", *Proc. Natl. Acad. Sci. USA*, 91: 5967–5971 (1994).

Geremia, et al., "Embolization of Experimentally Created Aneurysms with Intravascular Stent Devices", *AJNR*, 15: 1223–1231 (1994).

Gomez, et al., "Endovascular Theraphy of Traumatic Injuries of the Extracranial Cerebral Arteries", *Endovascular Therapy and Neurocritical Care* 15 (4): 789–809 (Oct., 1999).

Hemphili, III, et al., "Endovascular Therapy of Traumatic Injuries of the Intracranial Cerebral Arteries", *Endovascular Therapy and Neurocritical Care* 15 (4): 811–829 (Oct., 1999).

Jungreis, "The Use of Stents in Endovascular Intervention", *AJNR*, 16: 1976–1976 (1995).

Kinugasa, et al., "Direct Thrombosis of Aneurysms with Celluose Acetate Polymer", *J. Neurosurg.*, 77: 501–507 (1992).

Kinugasa, et al., "Early Treatment of Subarachnoid Hemorrhage After Preventing Rerupture of an Aneurysm", *J. Neurosurg.*, 83:34–41 (1995).

Kinugasa, et al., "Prophylactic Thrombosis to Prevent New Bleeding and to Delay Aneurysm Surgery", *Neurosurg.*, 36:661 (1995).

Kinugasa, et al., "Cellulose Acetate Polymer Thrombosis for the Emergency Treatment of Aneurysms: Angiographic Findings, Clinical Experience, and Histopathological Study", *Neurosurg.*, 34(4): 694–701(1994).

Laird, et al., "Inhibition of Neointimal Proliferation With Low–Dose Irradiation From a β–Particle Emiting Stent," *Circulation* 93(3):529–536 (1996).

Malek, et al., "Balloon–assist Technique for Endovascular Coil Embolization of Geometrically Difficult Intracranial Aneurysm", *Neurosurgery*, 46(6): 1397–1407 (2000).

Mandai, et al., "Direct Thrombosis of Aneurysms with Cellulose Acetate Polymer: Part I—Results of Thrombosis in Experimental Aneurysms", *J. Neurosurg.*, 77: 497–500 (1992).

Mericle, et al., "Stenting and Secondary Coiling of Intracranial Internal Carotid Artery Aneurysm: Technical Case Report", *Neurosurgery*, 43(5): 1229–1234 (1998).

Moret, et al., "The "Remodeling Technique" in the Treatment of Wide Neck Intracranial Aneurysms", *Interventional Neuroradiology*, 3: 21–35 (1997).

Nelson, et al., "Balloon–assisted Coil Embolization of Wide– Necked Aneurysms of the Internal Carotid Artery: Medium–term Angiographic and Clinical Follow–up in 22 Patients", *Am J. Neuroradiol.*, 22: 19–26 (2001).

Pierot, et al., "Endovascular Treatment of Post–Traumatic Complex Carotid–Cavernous Fistulas, Using the Arterial Approach", *J. Neuroradiol.*, 19: 79–87 (1992) (document presented in both English and French).

Popowski, et al., "Intra–Arterial $^{90}$Y Brachytherapy: Preliminary Dosimetric Study Using a Specially Modified Angioplasty Balloon", *Int. J. Radiation Oncology Biol. Phys.*, 33(3): 713–717 (1995).

Riina, et al. "Future Endovascular Management of Cerebral Aneurysms", *Neurosurgery Clinics of North America*, 9(4): 917–921 (1998).

Schopohl, et al., "$^{192}$IR Endovascular Brachytherapy for Avoidance of Intimal Hyperplasia After Percutaneous Transluminal Angioplasty and Stent Implantation in Peripheral Vessels: 6 Years of Experience", *Int. J. Radiation Oncology Biol. Phys.*, 36(4): 835–840 (1996).

Slepian, "Polymeric Endoluminal Paving: A Family of Evolving Methods for Extending Endoluminal Therapeutics Beyond Stenting", *Contemporary Interventional Techniques*12 (4): 715–737 (1994).

Slepian, et al. "Polymeric Endoluminal Gel Paving: Therapeutic Hydrogel Barriers and Sustained Drug Delivery Depots for Local Arterial Wall Biomanipulation." *Semin. Intervent. Cardiol.* 1: 103–116 (1996). (Article not enclosed herewith. Applicant will provide a copy as soon as possible after filing this IDS).

Slepian, et al., "$β_3$–Integrins Rather than $β_1$–Integrins Dominate Integrin–Matrix Interactions involved in Postinjury Smooth Muscle Cell Migration", *American Heart Association*, pp. 1818–1827, May 12, 1998.

Slepian, et al., "Pre–Conditioning of Smooth Muscle Cells via Induction of the Heat Shock Response Limits Proliferation Following Mechanical Injury", *Biochemical and Biophysical Research Communications*, 225: 600–607 (1996) (Article No. 1217).

Szikora, et al., "Endovascular Treatment of Experimental Aneurysms with Liquid Polymers: The Protective Potential of Stents", *Neurosurgery*, 38 (2): 339–347 (1996).

TAKI, et al., "Selection and Combination of Various Endovascular Techniques in the Treatment of Giant Aneurysms", *J. Neurosurg.*, 77:37–24 (1992).

Talja, et al., "Bioabsorbable and Biodegradable Stents in Urology", *Journal of Endourology*, 11 (6):391–397 (1997).

Violaris, et al., "Endovascular Stents: a "Break Through Technology", Future Challenges", *International Journal of Cardiac Imaging*, 13: 3–13 (1997).

Waksman, et al., "Local Catheter–Based Intracoronary Radiation Therapy for Restenosis", *Am. J. Cardiol.*, 78 (suppl 3A): 23–28 (1996).

Weill, et al., "Giant Aneurysms of the Middle Cerebral Artery Trifurcation Treated with Extracranial–Intracranial Arterial Bypass and Endovascular Occlusion", *J. Neurosurg.*, 89: 474–478 (1998).

* cited by examiner

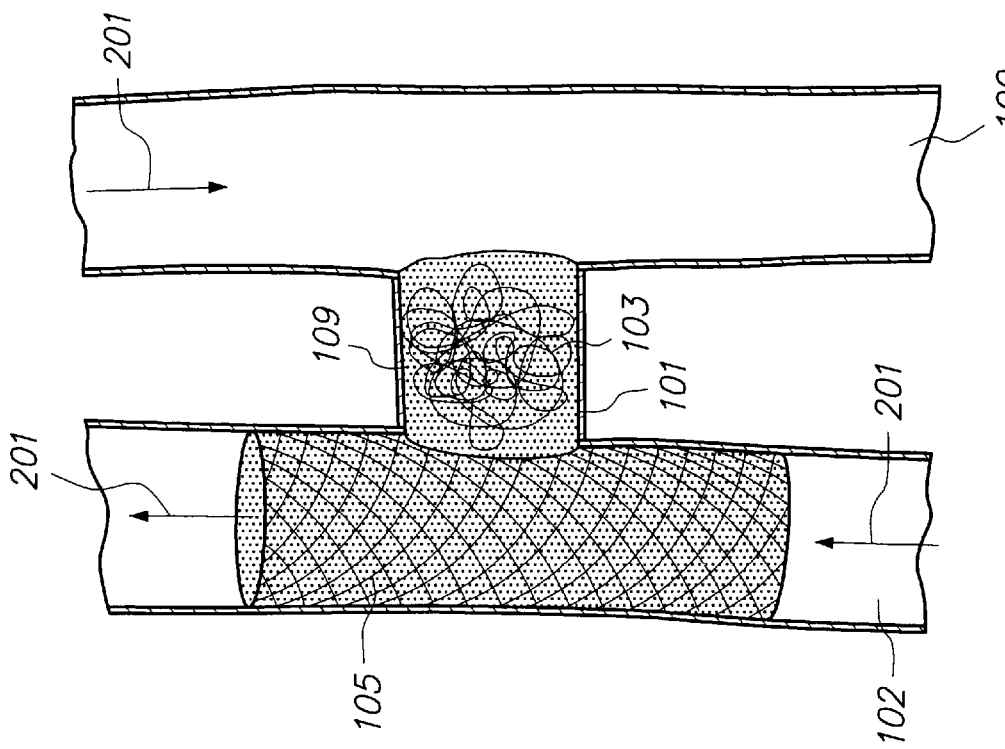
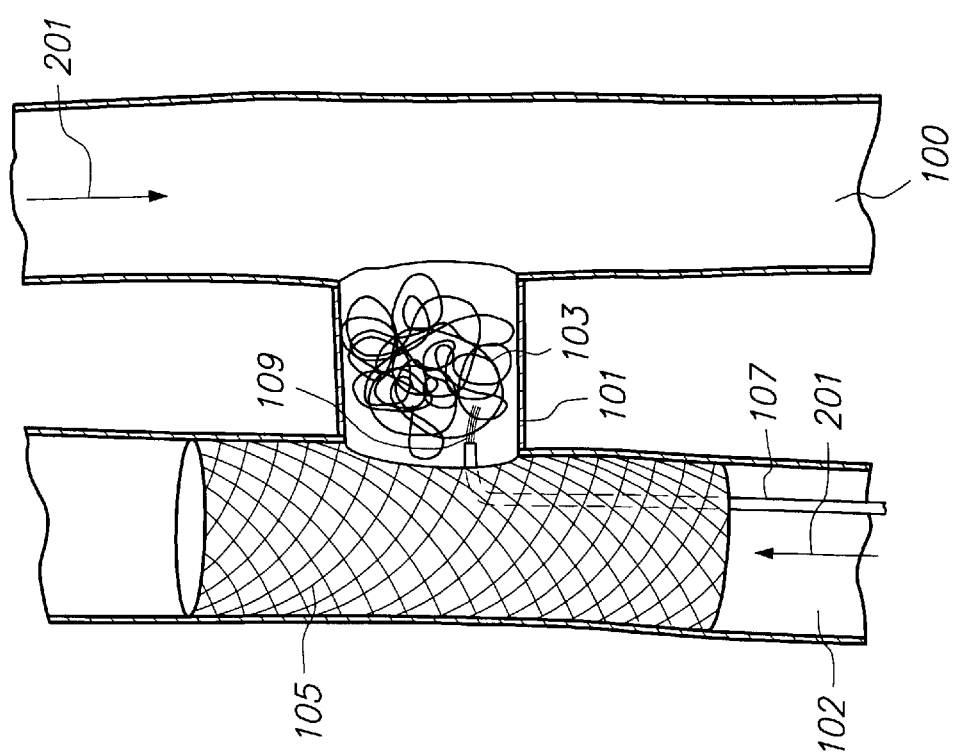

METHODS FOR VASCULAR RECONSTRUCTION OF DISEASED ARTERIES

CROSS REFERENCE TO RELATED APPLICATIONS

This application claims priority to U.S. Provisional patent application Ser. No. 60/249,342, filed Nov. 15, 2000 and U.S. Provisional patent application Ser. No. 60/252,757, filed Nov. 21, 2000, both of which are incorporated herein in their entirety.

BACKGROUND OF THE INVENTION

1. Field of the Invention

This invention is directed to methods of treating diseased, non-aneurysmal arteries with vascular reconstruction.

Specifically, the methods of this invention can be used to remodel blood flow pathways, redirect blood flow patterns, and to seal off undesired blood flow pathways. The methods of this invention can be used to treat a variety of diseased arteries in need of vascular reconstruction. For instance, the invention can be used to treat fistulas and other vascular abnormalities. In addition, the invention can be used to treat vascular walls which have suffered traumatic tears, punctures or dissections. The methods of this invention can also be used to treat or prevent stenosis in arteries which have undergone angioplasty. The present invention can even be used as an alternative to angioplasty.

REFERENCES

The following publications are cited in this application as superscript numbers:

1. Dunn, et al., U.S. Pat. No. 4,938,763 for "*Biodegradable In-Situ Forming Implants and Methods of Producing Same*", issued Jul. 3, 1990
2. Kinugasa, et al., "Direct Thrombois of Aneurysms with Cellulose Acetate Polymer", *J. Neurosurg.*, 77:501–507 (1992)
3. "*CANCER, Principles & Practice of Oncology*", 4th Ed., Volume 1, "*Cancer Treatment*", pp. 545–548 (1993)
4. Greff, et al., U.S. Pat. No. 5,667,767, for "Novel Compositions for Use in Embolizing Blood Vessels", issued Sep. 16, 1997
5. Greff, et al., U.S. Pat. No. 5,580,568 for "Cellulose Diacetate Compositions for Use in Embolizing Blood Vessels", issued Dec. 3, 1996
6. Kinugasa, et al., "Early Treatment of Subarachnoid Hemorrhage After Preventing Rerupture of an Aneurysm", *J. Neurosurg.*, 83:34–41 (1995)
7. Kinugasa, et al., "Prophylactic Thrombosis to Prevent New Bleeding and to Delay Aneurysm Surgery", *Neurosurg.*, 36:661 (1995)
8. Taki, et al., "Selection and Combination of Various Endovascular Techniques in the Treatment of Giant Aneurysms", *J. Neurosurg.*, 77:37–24 (1992)
9. Evans, et al., U.S. patent application Ser. No. 08/802,252 for "Novel Compositions for Use in Embolizing Blood Vessels", filed Feb. 19, 1997
10. Castaneda-Zuniga, et al., *Interventional Radiology*, in Vascular Embolotherapy, Part 1, 1:9–32, Williams & Wilkins, Publishers (1992)
11. Rabinowitz, et al., U.S. Pat. No. 3,527,224 for "Method of Surgically Bonding Tissue Together", issued Sep. 8, 1970
12. Hawkins, et al., U.S. Pat. No. 3,591,676 for "Surgical Adhesive Compositions", issued Jul. 6, 1971
13. Laird, et al., "Inhibition of Neointimal Proliferation With Low-Dose Irradiation From a β-Particle Emiting Stent," *Circulation* 93(3):529–536 (1996)
14 Greff, et al., U.S. patent application Ser. No. 08/962,819, *Radioactive Embolizing Compositions*, filed Nov. 3, 1997 now U.S. Pat. No. 6,015,541 which issued on Jan. 18, 2000.
15. Hemphill, III, et al., "Endovascular Therapy of Traumatic Injuries of the Intracranial Cerebral Arteries", *Endovascular Therapy and Neurocritical Care* 15 (4): 811–829 (October, 1999).
16. Gomez, et al., "Endovascular Theraphy of Traumatic Injuries of the Extracranial Cerebral Arteries", *Endovascular Therapy and Neurocritical Care* 15 (4):789–809 (October, 1999).

All of the above publications are herein incorporated by reference in their entirety to the same extent as if each individual reference was specifically and individually indicated to be incorporated herein by reference in its entirety.

2. State of the Art

Vascular reconstruction involves the non-endogenous reformation of arterial vessels in order to prophylactically or therapeutically treat one or more arterial disease conditions in a mammal. Examples of diseased arterial conditions include, for instance, high flow fistulas, dissections, and restenosis of the arterial endothelial wall after balloon angioplasty to treat atherosclerosis.

1. Dissections

Dissections occur when injury to one or more arterial layers allows blood to force its way along a dissection plane.[5] In the most common type of dissection, an injury or defect occurs in the intima layer of the blood vessel, causing blood to pool between the intima and media layers. The blood that collects below the intima layer may push it towards the interior of the lumen. The dissection may cause a flap of the intima to extend out into the lumen. This flap can collect embolic material or possibly even occlude the lumen.

In other instances, the dissection can occur between the media and adventicia layers. Here, the pooling of blood in the dissection can lead to either a subarachnoid hemorrhage or the formation of a pseudoaneurysm.[15]

2. Fistulas

Fistulas involve abnormal connections between arterial and venous circulations which can cause inadequate perfusion of affected tissue.[15] Fistulas can be "direct", meaning that there is a complete disruption of the wall of an artery, with connection directly into the venous circulation. Alternatively, fisulas can be "indirect", meaning that arteriovenous connections are located within the dura.

3. Atherosclerosis

In the case of atherosclerosis, this arterial disease involves thickening and hardening of the wall portions of the larger arteries of mammals. It is a life-threatening affliction that is largely responsible for coronary artery disease, aortic aneurysm and arterial disease of the lower extremities. Atherosclerosis also plays a major role in cerebral vascular disease. It is responsible for more deaths in the United States than any other disease.

Angioplasty has heretofore been a widely used method for treating atherosclerosis. Percutaneous transluminal coronary angioplasty (hereinafter "PTCA") procedures involve inserting a deflated balloon catheter through the skin and into the vessel or artery containing the stenosis. The catheter is then passed through the lumen of the vessel until it reaches the stenoic region, which is characterized by a build up of fatty streaks, fibrous plaques and complicated lesions on the vessel wall, which result in a narrowing of the vessel and blood flow restriction. In order to overcome the harmful narrowing of the artery caused by the atherosclerotic condition, the balloon is inflated, thus flattening the plaque against the arterial wall and otherwise expanding the arterial lumen.

Although PTCA has produced excellent results and low complication rates, there has, however, been difficulties associated with the use of this technique. In particular, during the expansion of the balloon against the arterial wall, the arterial wall is frequently damaged and injured. While this damage itself is not believed to be particularly harmful to the health or the life of the patient, the healing response triggered by this damage can cause a reoccurrence of the atherosclerotic condition. In particular, it has been observed that the smooth muscle cells associated with the stenotic region of the artery initiate cell division in response to direct or inflammatory injury of the artery.

Restenosis is the closure of a peripheral or coronary artery following trauma to the artery caused by efforts to open an occluded portion of the artery, such as, for example, by dilation, ablation, atherectomy or laser treatment of the artery. For these angioplasty procedures, restenosis occurs at a rate of about 20–50% depending on the vessel location, lesion length and a number of other variables. Restenosis is believed to be a natural healing reaction to the injury of the arterial wall that is caused by angioplasty procedures. The healing reaction begins with the clotting of blood at the site of the injury. The final result of the complex steps of the healing process is intimal hyperplasia, the migration and proliferation of medial smooth muscle cells, until the artery is again stenotic or occluded.

In an attempt to prevent restenosis, metallic intravascular stents have been permanently implanted in coronary or peripheral vessels. The stent is typically inserted by catheter into a vascular lumen and expanded into contact with the diseased portion of the arterial wall, thereby providing internal support for the lumen. However, it has been found that restenosis can still occur with such stents in place. Without being limited to any theory, it is believed that the in situ placed stent does not isolate the arterial wall from the oxygen/nutrients of the blood necessary for smooth muscle cell proliferation which is the seminal event in restenosis.

SUMMARY OF THE INVENTION

This invention is directed to methods of treating diseased, non-aneurysmal arteries with vascular reconstruction.

Specifically, in one embodiment, these methods entail placement of one or more stents in a diseased artery and subsequently delivering, in vivo, a fluidic composition under conditions wherein the fluidic composition forms a polymeric film which coats the diseased vascular wall and the stent thereby isolating the diseased portions of the artery from the systemic blood flow. Without being limited by any theory, it is believed that isolation of the diseased portions of the artery prevents blood contact with the vascular wall thereby denying oxygen, nutrients and the like to, for example, the smooth muscle tissue necessary to initiate restenosis or other diseased conditions. It is further believed that, over time, endothelialization of healthy arterial cells over the polymeric film will occur. Accordingly, the vascular reconstruction methods of this invention prevent further growth of the diseased portions of the artery and provide for endothelialization of healthy arterial cells over the stent and composition structure.

In another embodiment, a fluidic composition is delivered to the diseased vascular wall to in situ form a stent thereby isolating the diseased portion of the artery from the systemic blood flow. This vascular reconstruction prevents further growth of the diseased portions of the artery and provides for endothelialization of healthy arterial cells over the stent and composition structure.

In another embodiment, after the fluidic composition is delivered to the site of the diseased vascular artery, a balloon catheter is inserted at the vascular site and inflated. The inflation of the balloon catheter pushes the fluidic composition up against the vascular walls and (in situations where a mechanical stent is being used) into any recesses in the stent and any openings between the stent and the vascular walls. This action helps to conform the fluidic composition and resulting polymeric film to the contours of the vascular site.

The methods of this invention can be used to treat a variety of diseased arteries in need of vascular reconstruction. For instance, the invention can be used to treat fistulas and other vascular abnormalities. In addition, the invention can be used to treat vascular walls which have suffered traumatic tears, punctures or dissections.

The methods of this invention can also be used to treat or prevent restenosis in arteries which have undergone angioplasty. The present invention can even be used as an alternative to angioplasty.

Accordingly, in one of its method aspects, this invention is directed to a method for treating a diseased, non-aneurysmal artery in a mammalian patient which method comprises:

(a) identifying the vascular site of a diseased, non-aneurysmal artery in a mammalian patient wherein said vascular site participates in the systemic blood flow of said patient;

(b) inserting a stent into the diseased artery at the vascular site; and (c) delivering a fluidic composition to the vascular site which composition in situ forms a solid in and around the stent thereby isolating the vascular walls at the vascular site from systemic blood flow.

In another embodiment, the method further comprises:

(d) conforming the fluidic composition to the contours of the vascular site.

In a preferred embodiment, the stent employed is an open or mesh stent.

In another embodiment, steps (b) and (c) are combined such that the stent is formed in situ from the fluidic composition. In this embodiment, this invention is directed to a method for treating a diseased, non-aneurysmal artery in a mammalian patient which method comprises:

(a) identifying the vascular site of a diseased, non-aneurysmal artery in a mammalian patient wherein said vascular site participates in the systemic blood flow of said patient;

(b) delivering a fluidic composition to the vascular site under conditions where the composition in situ forms a solid film which adheres to the vascular wall thereby isolating the vascular site from systemic blood flow.

In another embodiment, the method further comprises:

(c) conforming the fluidic composition to the contours of the vascular site.

Optionally, non-particulate agents can be used along with the fluidic composition to fill in the spaces in and around the stent. The use of such non-particulate agents is particularly beneficial when the fluidic composition is being used to fill larger spaces or high flow regions, such as, for instance, fistulas. Such non-particulate agents preferably comprise metallic coils and, more preferably, platinum coils.

The stent and fluidic compositions of the present invention can also be delivered to the vascular site with a stent and balloon catheter.

Accordingly, in one of its method aspects, this invention is directed to a method for treating diseased, non-aneurysmal arteries by vascular reconstruction which method comprises:

(a) identifying the vascular site of a diseased, non-aneurysmal artery in a mammalian patient wherein said vascular site participates in that systemic blood flow of said patient;

(b) endovascularly delivering to a vascular site a stent and balloon catheter, said stent and balloon catheter comprising a catheter fitted with an inner, non-porous balloon, an outer, porous balloon, and an unexpanded stent encircling the catheter, the outer balloon and the inner balloon;

(c) inflating said inner balloon to expand the stent out to the vascular walls at said vascular site; and (d) delivering to the vascular site, through the porous outer balloon, a fluidic composition which composition in situ forms a solid in and around the stent thereby isolating the vascular walls at the vascular site from systemic blood flow, the pressure of the balloon conforming the fluidic composition to the contours of the vascular site.

In another embodiment, the stent is delivered to the vascular site in a separate step.

Accordingly, in one of its method aspects, this invention is directed to a method for treating diseased, non-aneurysmal arteries by vascular reconstruction which method comprises:

(a) identifying the vascular site of a diseased, non-aneurysmal artery in a mammalian patient wherein said vascular site participates in that systemic blood flow of said patient;

(b) endovascularly delivering to a vascular site an unexpanded stent;

(c) expanding the stent at the vascular site;

(d) delivering a fluidic composition to the vascular site which composition in situ forms a solid in and around the stent thereby isolating the vascular walls at the vascular site from systemic blood flow; and (e) conforming the fluidic composition to the contours of the vascular site.

In another embodiment, the fluidic composition is delivered to the vascular site by a balloon catheter.

Accordingly, in one of its method aspects, this invention is directed to a method for treating diseased, non-aneurysmal arteries by vascular reconstruction which method comprises:

(a) identifying the vascular site of a diseased, non-aneurysmal artery in a mammalian patient wherein said vascular site participates in that systemic blood flow of said patient;

(b) endovascularly delivering to a vascular site an unexpanded stent;

(c) expanding the stent at the vascular site;

(d) delivering a fluidic composition to the vascular site with a porous balloon catheter which composition in situ forms a solid in and around the stent thereby isolating the vascular walls at the vascular site from systemic blood flow; and (e) conforming the fluidic composition to the contours of the vascular site.

In another embodiment, the stent is delivered to the vascular site in a separate step, the fluidic composition is delivered to the vascular site through a catheter and a balloon catheter is used to conform the fluidic composition to the contours of the vascular site.

Accordingly, in one of its method aspects, this invention is directed to a method for treating diseased, non-aneurysmal arteries by vascular reconstruction which method comprises:

(a) identifying the vascular site of a diseased, non-aneurysmal artery in a mammalian patient wherein said vascular site participates in that systemic blood flow of said patient;

(b) endovascularly delivering to a vascular site an unexpanded stent;

(c) expanding the stent at the vascular site;

(d) delivering a fluidic composition to the vascular site with a catheter which composition in situ forms a solid in and around the stent thereby isolating the vascular walls at the vascular site from systemic blood flow; and (e) conforming, through the inflation of a balloon catheter, the fluidic composition to the contours of the vascular site.

The stents used in this invention can include, for example, a self expanding stent, such as a Nitrol self expanding stent, a stent which is expanded with the inflation of a balloon, or a stent which is triggered to expand when a sheath covering is slid back to release the stent.

Another aspect of this invention is directed to a kit of parts comprising:

(a) a first member which contains a composition comprising a water-insoluble biocompatible polymer, a biocompatible solvent and a contrast agent; and (b) a stent.

The biocompatible polymer employed in this kit can be either a biodegradable polymer or a non-biodegradable polymer but is, preferably, a non-biodegradable polymer.

Another aspect of this invention is directed to a kit of parts comprising:

(a) a first member which contains a composition comprising a water-insoluble biocompatible polymer, a biocompatible solvent and a contrast agent; and (b) a stent and balloon catheter. This stent and balloon catheter comprises a catheter fitted with an inner, non-porous balloon, an outer, porous balloon, and an unexpanded stent encircling the catheter, the outer balloon and the inner balloon.

The biocompatible polymer employed in this kit can be either a biodegradable polymer or a non-biodegradable polymer but is, preferably, a non-biodegradable polymer.

Another aspect of this invention is directed to a kit of parts comprising:

(a) a first member which contains a composition comprising a water-insoluble biocompatible polymer, a biocompatible solvent and a contrast agent;

(b) a stent;

(c) a non-porous balloon catheter; and (d) a catheter for delivery of fluidic composition.

The fluidic composition employed in the methods of this invention preferably comprises a biocompatible polymer. When a biocompatible polymer is employed, the fluidic composition preferably comprises a biocompatible polymer, a biocompatible contrast agent, and a biocompatible solvent which solubilizes the biocompatible polymer wherein sufficient amounts of the polymer are employed in the composition such that, upon delivery to the vascular site of the diseased artery, a polymer precipitate forms which coats the vascular wall of the diseased artery and the stent with a solid polymeric film thereby isolating the diseased portions of the artery from the systemic blood flow as the fluidic composition solidifies.

Such polymer composition can comprise, for example, a biocompatible polymer at a concentration of from about 2.5 to about 25 weight percent, and more preferably from about 4 to about 20 weight percent; a biocompatible contrast agent at a concentration of from about 10 to about 40 weight percent, and more preferably from about 20 to 30 weight percent; and a biocompatible solvent which makes up the remainder of the composition, wherein the weight percent of the biocompatible polymer, contrast agent and biocompatible solvent is based on the total weight of the complete composition.

In a preferred embodiment, the biocompatible solvent is dimethylsufoxide (DMSO), ethanol, ethyl lactate or acetone.

When used in combination with a stent, the fluid composition can comprise a biocompatible prepolymer, a contrast agent and optionally a biocompatible solvent.

The stent employed in the present invention can either be formed in situ or placed in the artery by microcatheter techniques.

Alternatively, a stent and balloon catheter allows for the placement of the stent at the vascular site.

In either case, the mechanisms of this invention entail the non-endogenous isolation of the diseased arterial wall to the systemic blood flow. This vascular reconstruction prevents further growth of the diseased portions of the artery and provides for endothelialization of healthy arterial cells over the stent and fluidic composition structure.

BRIEF DESCRIPTION OF THE DRAWINGS

FIG. 1 is a schematic side view of an H-shaped fistula where a mesh stent has been placed in an artery next to the fistula and a fluidic composition is being filled into the fistula cavity with a microcatheter.

FIG. 2 is a schematic side view of an H-shaped fistula where the fluidic composition has filled the fistula cavity and coated the stent and the diseased portions of the artery, isolating the diseased portions of the artery from systemic blood flow.

DETAILED DESCRIPTION OF THE INVENTION

Figure 3:
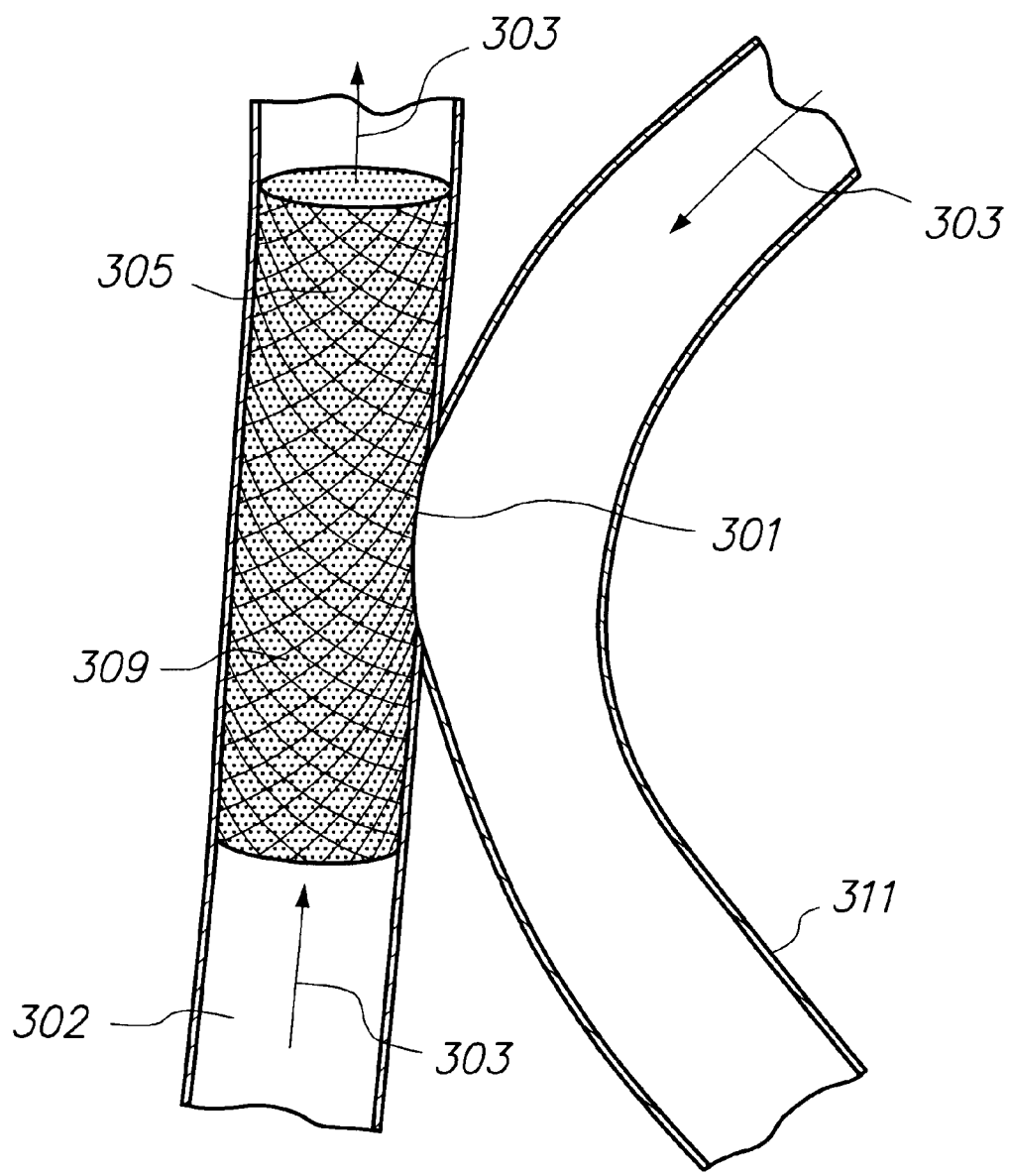
FIG. 3 is a schematic side view of a fistula where the fluidic composition has filled the fistula cavity and coated the stent and the diseased portions of the artery, isolating the diseased portions of the artery from systemic blood flow.

This invention is directed to methods of treating diseased, non-aneurysmal arteries with vascular reconstruction. Specifically, in one embodiment, these methods entail placement of one or more stents in a diseased artery and delivering, in vivo, a fluidic composition under conditions wherein the fluidic composition forms a polymeric film which coats the diseased vascular wall and the stent thereby isolating diseased portions of the artery from the systemic blood flow as the fluidic composition solidifies. Without being limited by any theory, it is believed that isolation of the diseased portions of the artery prevents blood contact with the vascular wall thereby denying oxygen, nutrients and the like to, for example, the diseased vascular tissue. It is further believed that, over time, endothelialization of healthy arterial cells over the polymeric film will occur. Accordingly, the vascular reconstruction methods of this invention prevent further growth of the diseased portions of the artery and provide for endothelialization of healthy arterial cells over the stent and composition structure.

However, prior to discussing this invention in further detail, the following terms will first be defined:

The term "biocompatible polymer" refers to polymers which, in the amounts employed, are non-toxic and substantially non-immunogenic when used internally in the patient and which are substantially insoluble in the body fluid of the mammal. The biocompatible polymer can be either biodegradable or, preferably, non-biodegradable.

Biodegradable polymers are disclosed in the art.[1,3] For example, Dunn, et al.[1] discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, and copolymers, terpolymers and combinations thereof. Other biodegradable polymers include, for example, fibrin, gelatin, collagen, etc.

Suitable non-biodegradable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9].

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by, e.g., injection. Such factors are well within the skill of the art. Suitable high viscosity compositions and methods for delivery are disclosed in U.S. patent Ser. No. 09/574,379, filed May 19, 2000.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by merely adjusting the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. For ease of injection, the ethylene vinyl alcohol copolymer composition is preferably selected such that a solution of 5 weight percent of the ethylene vinyl alcohol copolymer, 20 weight percent of a tantalum contrast agent in DMSO has a viscosity equal to or less than 60 centipoise at 20° C. As is apparent to one skilled in the art, with all other facts being equal, copolymers having a lower molecular weight will impart a lower viscosity to the composition as compared to higher molecular weight copolymers. Accordingly, adjustment of the viscosity of the composition as necessary for catheter delivery can be readily achieved by merely adjusting the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous environment (e.g., blood or tissue). In a particularly preferred embodiment, the copolymers employed herein comprise a mole percent of ethylene of from about 25 to about 60 and a mole percent of vinyl alcohol of from about 40 to about 75. Even more preferably, the copolymers employed herein comprise a mole percent of ethylene of from about 38 to about 48 and a mole percent of vinyl alcohol of from about 52 to 62. These compositions provide for requisite precipitation rates suitable for use in the methods described therein.

The term "contrast agent" refers to a biocompatible radiopaque material capable of being monitored during injection into a mammalian subject by, for example, radiography. The contrast agent can be either water soluble or water insoluble and preferably does not contain radioactivity above the native or endogenous amounts naturally occurring in the elements employed (i.e., are "non-radioactive").

Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a preferred particle size of about 10 μm or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, ethyl lactate, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic and substantially non-immunogenic when used internally in the patient and which are substantially insoluble in blood. Suitable biocompatible prepolymers include, by way of example, urethanes, cyanoacrylates[10,11,12], (C1–C6)hydroxyalkyl (C1–C6) alkacrylate (e.g., hydroxyethyl methacrylate), silicone prepolymers, and the like. The prepolymer can either be a monomer or a reactive oligomer[12]. Preferably, the biocompatible prepolymer does not cause an adverse inflammatory reaction when employed in vivo.

A "stent" is a device which retains integrity of the vascular wall or body lumen when it is placed in contact with or when it is formed in situ adjacent to or in contact with a vascular wall. A stent functions to maintain patency of a body lumen (such as a vascular wall) and is especially used as an implant in blood vessels. Stents may be utilized after atherectomy, which excises plaque, or cutting balloon angioplasty, which scores the arterial wall prior to dilatation, to maintain acute and long-term patency of the vessel. Stents may be utilized in by-pass grafts as well, to maintain vessel patency. Stents can also be used to reinforce collapsing structures in the respiratory, biliary, urological, and other tracts. Effectively, a stent overcomes the natural tendency of the vessel walls of some patients to close back down, thereby maintaining a more normal flow of blood through that vessel than would otherwise be possible if the stent were not in place.

Suitable stents include open, lattice or porous stents in which the structure of the stent is mesh-like in nature having one or more openings or pores ("open or mesh stent"). The size of at least one of the openings in the stent is preferably large enough to permit a catheter to pass through the stent. Openings of about 0.2 to about 10 mm are preferred for traversal of the catheter through the opening, and more preferably about 1.0 to about 3.0 mm.

Alternatively, stents having one or more grooves (e.g., chevrons) on the surface such that there are cavities created between the stent and the arterial wall can also be employed in the methods of this invention.

Suitable stents can be cylindrical, tapered, dumbbell or otherwise shaped to fit the necessary vascular contours. Commercially available stents which can be used with this invention include (but are not limited to): the Wallstent, the Strecker Stent, the Palmaz-Schatz stent, the Wiktor stent, the AVE Micro Stent, and the Multilink stent.

"Restenosis" is the closure of an artery following trauma to the artery caused by efforts to open an occluded portion of the artery, such as, for example, by dilation, ablation, atherectomy or laser treatment of the artery. Restenosis is believed to be a natural healing reaction to the injury of the arterial wall that is caused by angioplasty procedures. The healing reaction begins with the clotting of blood at the site of the injury. The final result of the complex steps of the healing process is intimal hyperplasia, the migration and proliferation of medial smooth muscle cells, until the artery is again stenotic or occluded.

The term "inhibiting restenosis" or "inhibit restenosis" means that restenosis is inhibited from occurring or is reduced or less pronounced in its effect. In other words, the extent of restenosis is reduced, decreased or eliminated.

A "liquid permeable balloon" is a balloon which comprises at least a portion of a permeable balloon membrane which membrane allows the passage, under positive pressure, of a composition comprising a biocompatible polymer, a biocompatible solvent and a contrast agent. The permeable balloon membrane is preferably selected to allow the passage of insoluble particles having a particle size no larger than 10 $\mu$m. The positive pressure employed is preferably at least 5 atmospheres, more preferably 5 to 75 atmospheres, still more preferably 5 to 30 atmospheres, and even still more preferably 5 to 20 atmospheres. The permeable material employed in the balloon is not critical provided that it meets the above criteria. Such materials include, by way of example, expanded polytetrafluoroethylene (PTFE, tradename Gortex™), polyethyleneterephthalate (Dacron™, DuPont, Wilmington, Del.), and polyethylene with laser drilled openings. Liquid permeable balloons are also described by Raccini, et al.[10]

"Non-endogenously isolating the arterial walls of the diseased artery" refers to procedures for isolating the arterial walls of the diseased artery from systemic blood flow which procedures do not rely solely upon formation of biological tissue to effect complete isolation of the diseased arterial walls. In this regard, growth of endogenous tissue, e.g., over a stent, to isolate the diseased artery from blood circulation often occurs weeks after placement of the stent during which time the diseased arterial wall can grow beyond the scope of the stent.

"Solidification" refers to the in situ formation of a solid mass whether by the in situ polymerization of a prepolymer in the fluid composition or the precipitation of the polymer in the fluid composition or other means. Other means of polymer precipitation may include changes in temperature, ionic strength, addition of precipitating agents and the like.

Compositions

The polymer or prepolymer compositions employed in the methods of this invention are preferably first prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 25 weight percent of the biocompatible polymer composition based on the total weight of the polymer composition and more preferably from about 4 to about 20 weight percent. If necessary, gentle heating and stirring can be used to effect dissolution of the biocompatible polymer into the biocompatible solvent, e.g., 12 hours at 50° C.

A sufficient amount of a contrast agent is then added to the composition to achieve the effective concentration for the complete composition. Preferably, the composition will comprise from about 5 to about 40 weight percent of total contrast agent, and still more preferably from about 20 to 30 weight percent.

The biocompatible solvent preferably comprises the rest of the polymer composition. Accordingly, the solvent preferably comprises from about 35 to about 90 weight percent of the composition based on the total weight of the composition and more preferably about 50 to about 75 weight percent.

When a water soluble contrast agent is employed, the agent is typically soluble in the solution comprising the non-aqueous solvent and stirring is effected to render the composition homogeneous.

When a water insoluble contrast agent is employed, the agent is insoluble in the biocompatible solvent, and stirring is employed to effect homogeneity of the resulting suspension. In order to enhance formation of the suspension, the particle size of the water insoluble contrast agent is preferably maintained at about 10 $\mu$m or less and more preferably at from about 1 to about 5 $\mu$m (e.g., an average size of about 2 $\mu$m).

In one embodiment, a contrast agent having a particle size of less than 10 $\mu$m is prepared, for example, by fractionation. In such an embodiment, a water insoluble contrast agent such as tantalum, having an average particle size of less than about 20 $\mu$m, is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition can be heat sterilized and then stored preferably in sealed bottles or vials until needed.

Each of the polymers recited herein is commercially available or can be prepared by methods well known in the art. For example, polymers are typically prepared by conventional techniques such as radical, thermal, UV, γ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Prepolymer compositions can be prepared by adding sufficient amounts of any contrast agent employed in the liquid (e.g., liquid prepolymer) to achieve the effective concentration for the complete polymer composition. Preferably, the total contrast agent will comprise from about 7 to about 40 weight percent of the prepolymer composition based on the total weight of the composition and more preferably from about 14 to about 30 weight percent and even more preferably about 22 weight percent.

When a contrast agent is used which is not soluble in the biocompatible prepolymer composition, stirring is employed to effect homogeneity of the resulting suspension. In order to enhance formation of the suspension, the particle size of the insoluble contrast agent is preferably maintained at about 10 μm or less and more preferably at from about 1 to about 5 μm (e.g., an average size of about 2 μm).

When the prepolymer is liquid (as in the case of cyanoacrylates or silicone), the use of a biocompatible solvent is not strictly necessary but may be preferred to provide for an appropriate viscosity, for an appropriate curing time, etc. in the composition. Preferably, when employed, the biocompatible solvent will comprise from about 30 to about 90 weight percent of the biocompatible prepolymer composition based on the total weight of the prepolymer composition and more preferably from about 30 to about 70 weight percent. When a biocompatible solvent is employed, the prepolymeric composition typically comprises from about 10 to about 50 weight percent of the prepolymer based on the total weight of the composition, and more preferably from about 20 to about 60 weight percent.

Suitable solvents include iodinated soy bean or poppy seed oil for cyanoacrylates and water for hydroxyacrylics such as hydroxyethyl methacrylate. In such cases, the oil acts both as a carrier for the prepolymer, a contrast agent and a polymerization time modifier. Other solvents include hexamethyldisiloxane which is preferably employed in conjunction with silicone.

In a particularly preferred embodiment, the prepolymer is a cyanoacrylate which is preferably employed in a 1:1 ratio with an iodinated oil. When so employed, the cyanoacrylate adhesive is selected to have a viscosity of from about 5 to about 40 centipoise at 20° C.

Methods

This invention is directed to methods of treating diseased, non-aneurysmal arteries with vascular reconstruction.

In one embodiment, this vascular reconstruction is accomplished by placing a stent at the vascular site of the diseased artery, and subsequently delivering, in vivo, a fluidic composition under conditions which coat the diseased vascular wall and the stent with a solid polymeric film thereby isolating the diseased portions of the artery from the systemic blood flow as the fluidic composition solidifies. Optionally, the fluidic composition is conformed to the surface of the vascular site and the stent by the expansion of a balloon catheter at the vascular site.

In another embodiment, a fluidic composition is delivered to the diseased vascular wall to in situ form a stent thereby isolating the diseased portion of the artery from the systemic blood flow. Optionally, the fluidic composition is conformed to the surface of the vascular site by the expansion of a balloon catheter at the vascular site.

The vascular reconstruction of the present invention prevents further growth of the diseased portions of the artery and provides for endothelialization of healthy arterial cells over the polymeric film formed from the solidified fluidic composition.

The treatment protocol includes assessing the vascular site and determining the exact nature of vascular reconstruction needed by the patient.

In one embodiment of the invention, the method employs conventional endovascular techniques to provide a stent and balloon catheter at the vascular site. This stent and balloon catheter comprises a catheter fitted with an inner, non-porous balloon, an outer, porous balloon, and an unexpanded stent encircling the catheter, the outer balloon and the inner balloon. The inner balloon is inflated, expanding the stent against the vascular walls. Then, a fluidic composition is delivered to the outer balloon. The fluidic composition permeates the outer balloon at the porous region of the outer balloon, coating the stent and the vascular walls at the vascular site. The pressure of the inflated inner balloon serves to conform the fluidic composition to the contours of the vascular site.

In another embodiment of the invention, the method employs endovascular techniques to provide an unexpanded stent at the vascular site. The stent is expanded against the arterial walls at the vascular site. The stent can be self expanding, or expanded by, for example, inflation of a balloon catheter. Then, a balloon catheter is placed at the selected vascular site. The balloon catheter comprises a catheter fitted with an non-porous inner balloon and an outer balloon. The outer balloon has a porous region which is permeable to the fluidic composition. Positive pressure is generated within the inner balloon which inflates the inner balloon and pushes the outer balloon against the sides of the stent and the vascular walls. The fluidic composition is delivered to the outer balloon and permeates the porous region of the outer balloon, coating the stent walls and the vascular walls at the vascular site. The pressure of the inflated inner balloon serves to conform the fluidic composition to the contours of the vascular site.

In another embodiment of the invention, the method employs endovascular techniques to provide an unexpanded stent at the vascular site. The stent is expanded against the arterial walls at the vascular site. The stent can be self expanding, or expanded by, for example, inflation of a balloon catheter. Fluidic composition is delivered to the vascular site and the stent through a conventional endovascular catheter techniques. A balloon catheter is inserted at the vascular site and inflated to conform the fluidic composition to the contours of the vascular site.

When the fluidic composition is introduced in vivo at the vascular site, the biocompatible solvent diffuses rapidly into the body fluid and a solid, non-migratory precipitate or solid mass forms which precipitate is the water insoluble polymer and contrast agent encapsulated therein. Without being limited to any theory, it is believed that initially, solid mass forms upon contact with the body fluid.

When the method includes the placement of a stent at the vascular site of the diseased artery and a prepolymeric composition is introduced in vivo, the prepolymer rapidly polymerizes in situ (preferably in less than 15 minutes and more preferably in less than 5 minutes) and a solid non-migratory mass forms which mass is the water insoluble polymer and contrast agent encapsulated therein.

In either case, a solid non-migratory mass forms in situ coating the vascular walls and the stent at the vascular site. Depending on the nature of the diseased vasculature, the mass will also be deposited in one or more vascular deviations, holes, tears, dissections, or fistula. The size and thickness of the coating will depend on the nature of the diseased tissue and can be determined by one skilled in the art. The thickness of the layer should not significantly or substantially reduce the vessel lumen of the diseased artery.

If a balloon catheter is used, either to apply the fluidic composition or to conform the fluidic composition to the contours of the vascular site, the size and thickness of the coating will relate directly to the size and permeability of the balloon selected as well as the extent and duration of positive pressure maintained on the inflated balloon. Such factors are well within the skill of the art. Preferably, the coating thicknesses formed by the methods of this invention range from about 0.05 mm to about 0.5 mm.

Where non-particulate agents such as metallic coils are used to fill in spaces in and around the stent at the vascular site, such non-particulate agents should be packed into the selected space until there is a significant reduction in blood flow to the selected space, as can be determined by contrast injection under fluoroscopy.

Kits of Parts

Another embodiment of this invention is a kit of parts comprising a water-insoluble biocompatible polymer, a biocompatible solvent, and a stent. In a preferred embodiment, the biocompatible solvent is dimethylsulfoxide or ethyl lactate.

In an alternative embodiment, the kit of parts comprises a biocompatible prepolymer, and a stent.

Still another embodiment of this invention is a kit of parts comprising a water-insoluble biocompatible polymer, a biocompatible solvent, and a stent and balloon catheter. Optionally, this kit can further include a catheter suitable for delivering fluidic composition. In a preferred embodiment, the biocompatible solvent is dimethylsulfoxide or ethyl lactate.

Utility

The methods described herein are useful for treating diseased, non-aneurysmal arteries with vascular reconstruction. In these methods, a fluidic composition is delivered to a vascular site by known endovascular catheter techniques in a sufficient amount to fill in undesired vascular deviations, such as tears, ruptures, fistula, dissections, and the like. The fluidic composition also coats the diseased vascular site and, if used, a stent, isolating the diseased portions of the artery from the systemic blood flow. This vascular reconstruction prevents further growth of the diseased portions of the artery and provides for endothelialization of healthy arterial cells over the stent and composition structure. Accordingly, these compositions find use in human and other mammalian subjects in need of vascular reconstruction.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc = | cubic centimeter |
| DMSO = | dimethylsulfoxide |
| EVOH = | ethylene vinyl alcohol copolymer |
| g = | gram |
| kg = | kilogram |
| mg = | milligram |
| mL = | milliliter |
| OD = | outer diameter |

Example 1

The purpose of this example is to demonstrate the preparation of a fluid polymer composition useful in the methods of this invention.

Specifically, an EVOH polymer composition was prepared as follows:

Composition

A) 8 g EVOH (48 mole % ethylene);
B) 30 g tantalum having an average particle size of about 3 μm (narrow size distribution); and
C) 100 mL DMSO (anhydrous).

Component A) was added to Component C) at 50° C. and stirred for 2 hrs on a hot plate under an argon blanket. To this resulting composition was added Component B) and the resulting mixture was mixed until homogeneous.

Example 2

The purpose of this example is to demonstrate the preparation of a fluid polymer composition useful in the methods of this invention.

Specifically, an EVOH polymer composition was prepared as follows:

Composition

A) 16 g EVOH (48 mole % ethylene);
B) 30 g tantalum having an average particle size of about 3 μm (narrow size distribution); and
C) 100 mL DMSO (anhydrous).

Component A) was added to Component C) at 50° C. and stirred for 3 hrs on a hot plate under an argon blanket. To this resulting composition was added Component B) and the resulting mixture was mixed until homogeneous.

Example 3

Vascular Reconstruction of an H-Shaped Fistula

The purpose of this example is to demonstrate procedures which can be used to treat diseased, non-aneurysmal arteries with vascular reconstruction. In this example, vascular reconstruction of an H-Shaped Fistula is demonstrated.

As shown in FIG. 1, an H-Shaped Fistula has been identified for vascular reconstruction. Prior to vascular reconstruction, the vein (100), the fistula cavity (101) and the adjoining diseased artery (102) participate in the systemic blood flow (201) of the patient. Microcatheter techniques are used to deliver a mesh stent (105) to the diseased artery at the site of the desired vascular reconstruction. Such techniques can include, but are not limited to, (1) delivering a self-expanding stent to the vascular site, (2) delivering a stent and balloon catheter to the site and inflating the balloon to expand the stent or (3) triggering stent expansion by sliding back a sheath to release the stent. The mesh stent will serve as a framework for the new systemic blood flow which will be excluded from the fistula cavity.

Microcatheter (107) is then inserted into the diseased artery (102), through the middle of the cylindrical mesh stent (105), and threaded out through one of the openings in the mesh stent into the fistula cavity(101). Microcatheter techniques are then used to deliver non-particulate agents such as coils (103) to the fistula cavity (101). The same or a different catheter can be used to deliver fluidic composition (109) into the fistula cavity filling in the space around the coils and anchoring the coils in place.

Then, the fluidic composition is coated over the sides of the vascular walls of the diseased artery and the sides of the stent. This coating can be accomplished with the use of a permeable balloon catheter, such as a CVD Periflow catheter, which is inserted in the diseased artery, inside the cylindrical portion of the mesh stent (105) and inflated. The permeable balloon is expanded at the selected site, and fluidic composition flows out of the permeable balloon and coats the walls of the diseased artery and the stent. In addition, the pressure of the balloon against the layer of the fluidic composition helps to conform the fluidic composition to the contours of the vascular wall and the mesh stent.

The fluidic composition then solidifies into a solid polymeric film, isolating the diseased portions of the artery from the systemic blood flow.

As depicted in FIG. 2, systemic blood flow (201) will now pass through the inside of the coated stent, bypassing the fistula cavity (101). The vascular reconstruction will prevent further growth of the diseased portions of the artery and provide for endothelialization of healthy arterial cells over the coated stent.

Alternatively, the vascular reconstruction demonstrated in this example could have been performed by use of a stent and balloon catheter or by use of a stent, a catheter to deliver the fluidic composition to vascular site, and a non-porous balloon catheter to conform the fluidic composition to the contours of the vascular site.

Example 4

Vascular Reconstruction of K-Shaped Fistula

The purpose of this example is to demonstrate procedures which can be used to treat diseased, non-aneurysmal arteries with vascular reconstruction. In this example, vascular reconstruction of a K-Shaped Fistula is demonstrated.

As shown in FIG. 3, a K-Shaped Fistula has been identified for vascular reconstruction. Prior to vascular reconstruction, the fistula (301), the vein (311) and the adjoining diseased artery (302) participate in the systemic blood flow (303) of the patient. Microcatheter techniques are used to insert a mesh stent (305) into the diseased artery at the site of the desired vascular reconstruction. Such techniques can include, but are not limited to, (1) delivering a self-expanding stent to the vascular site, (2) delivering a stent and balloon catheter to the site and inflating the balloon to expand the stent, or (3) triggering stent expansion by sliding back a sheath to release the stent. The mesh stent serves as a framework for the new vascular blood flow which will exclude the fistula cavity.

A microcatheter (not shown) is then inserted into the diseased artery, through the middle of the cylindrical mesh stent (305) and threaded out through one of the openings in the mesh stent into the fistula. Fluidic composition (309) flows out of the microcatheter into the fistula filling it.

Then, the fluidic composition is coated over the sides of the vascular walls of the diseased artery and the sides of the stent. This coating can be accomplished with the use of a permeable balloon catheter which is inserted in the diseased artery, inside the cylindrical portion of the mesh stent (305) and inflated. The permeable balloon is expanded at the selected site, and the fluidic composition flows out of the permeable balloon and coats the walls of the diseased artery and the sides of the stent. As the inflated balloon presses against this layer of fluidic composition, the balloon conforms the fluidic composition to the contours of the vascular wall and the mesh stent.

The fluidic composition then solidifies into a solid polymeric film, isolating the diseased portions of the artery from the systemic blood flow.

After this vascular reconstruction, systemic blood flow (303) will now pass through the inside of the coated stent, bypassing the fistula cavity. The vascular reconstruction will prevent further growth of the diseased portions of the artery and provide for endothelialization of healthy arterial cells over the coated stent.

Alternatively, the vascular reconstruction demonstrated in this example could have been performed by use of a stent and balloon catheter or by use of a stent, a catheter to deliver the fluidic composition to vascular site, and a non-porous balloon catheter to conform the fluidic composition to the contours of the vascular site.

Example 5

Vascular Reconstruction of Dissections

The purpose of this example is to demonstrate procedures which can be used to treat diseased, non-aneurysmal arteries with vascular reconstruction. In this example, vascular reconstruction of a dissected artery is demonstrated.

Figure 4:
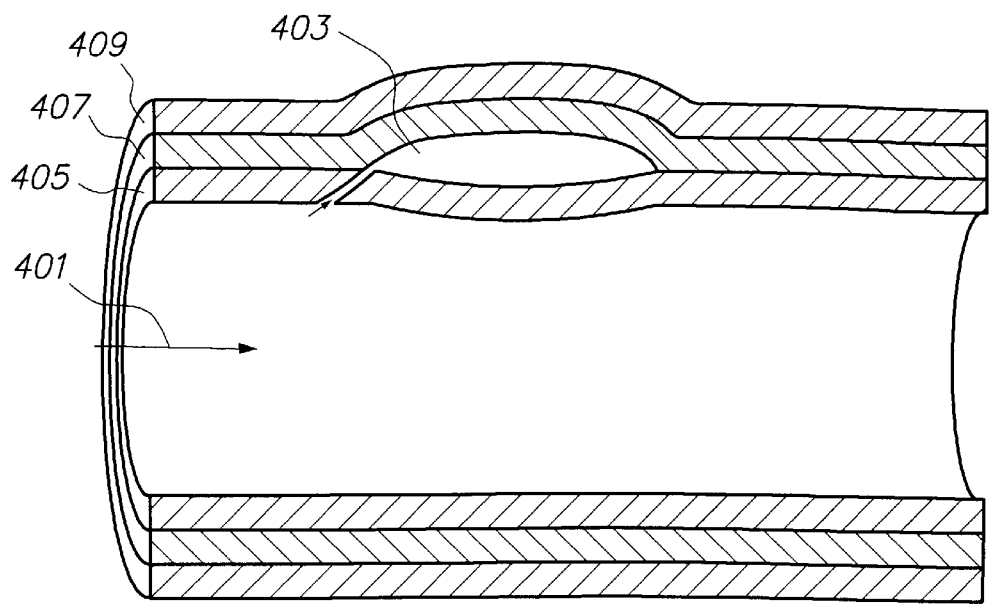
FIG. 4 is a schematic side view of a diseased artery where systemic blood is flowing into a dissection between the intima and media layers.

As shown in FIG. 4, a dissected artery has been identified for vascular reconstruction. Prior to vascular reconstruction, systemic blood flow (401) is passing through the center of the diseased artery as well as dissection (403). Dissection (403) has formed between the intima (405) and media (407) layers of the diseased artery. (Dissections can also found, for instance, between the media (407) and the adventicia (409) layers). Left untreated, blood is likely to pool in the dissections, pushing out the layers of the blood vessel wall. This pocket of blood can create a pseudoaneurysm and could cause blockage of the main artery.

Figure 5:
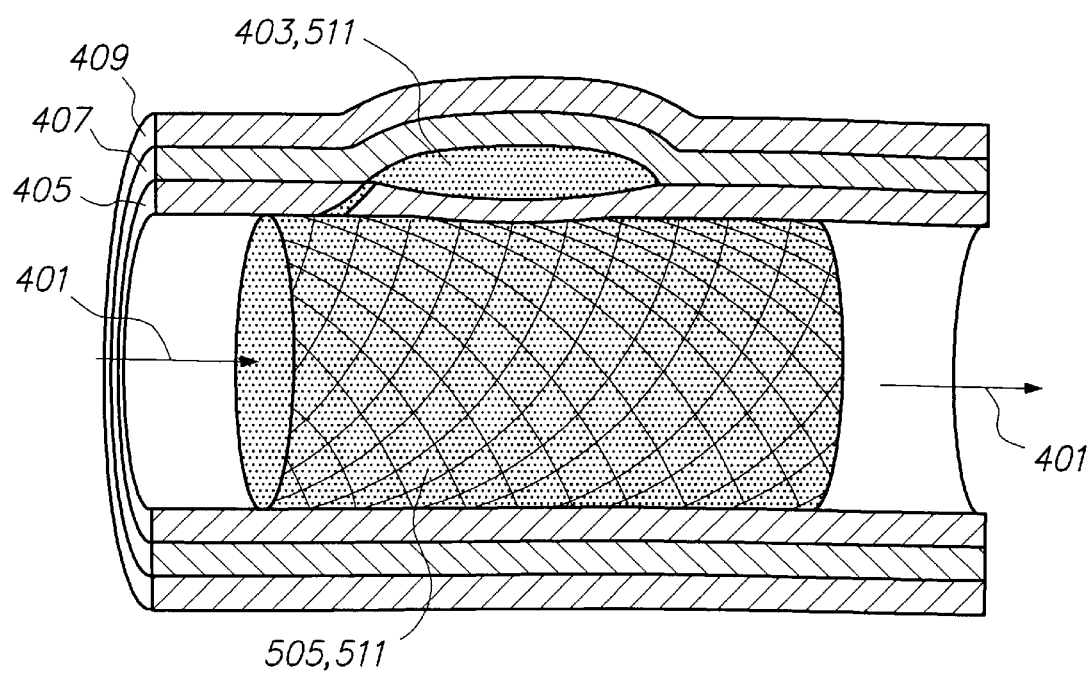
FIG. 5 is a schematic side view of a diseased artery where the fluidic composition has filled the dissection and coated the stent and the diseased portions of the artery, isolating the diseased portions of the artery from systemic blood flow.

Microcatheter techniques are used to insert a mesh stent (505) into the diseased artery at the site of the desired vascular reconstruction (see FIG. 5). Such techniques can include, but are not limited to, (1) delivering a self-expanding stent to the vascular site, (2) delivering a stent and balloon catheter to the site and inflating the balloon to expand the stent, or (3) triggering stent expansion by sliding back a sheath to release the stent. The mesh stent serves as a framework for the new vascular blood flow which will exclude dissection (403).

A microcatheter (not shown) is then inserted into the diseased artery, through the middle of the cylindrical mesh stent (505) and threaded out through one of the openings in the mesh stent into dissection (403). Fluidic composition (511) flows out of the microcatheter into the disection filling it.

Then, the microcatheter is used to coat the fluidic composition (511) over the sides of the vascular walls of the diseased artery and the sides of the stent. A non-porous balloon catheter can be inserted inside the cylindrical portion of the mesh stent (505) and inflated, conforming the fluidic composition to the contours of the vascular wall and the mesh stent.

The fluidic composition then solidifies into a solid polymeric film, isolating the diseased portions of the artery from the systemic blood flow.

After this vascular reconstruction, systemic blood flow (401) will now pass through the inside of the coated stent, bypassing dissection (403) (which is now filled with fluidic composition (511)). The vascular reconstruction will prevent further growth of the diseased portions of the artery and provide for endothelialization of healthy arterial cells over the coated stent.

Alternatively, the vascular reconstruction demonstrated in this example could have been performed by use of a stent and balloon catheter or by use of a stent and, to deliver the fluidic composition to the vascular site, a porous balloon catheter.

Example 6

Vascular Reconstruction of Stenoic Artery and Demonstration of Stent and Balloon Catheter The purpose of this example is to demonstrate procedures which can be used to treat diseased, non-aneurysmal arteries with vascular reconstruction. In this example, vascular reconstruction of a stenoic artery is demonstrated with a stent and balloon catheter. Such vascular reconstruction can be done immediately post balloon angioplasty or instead of angioplasty.

Figure 6:
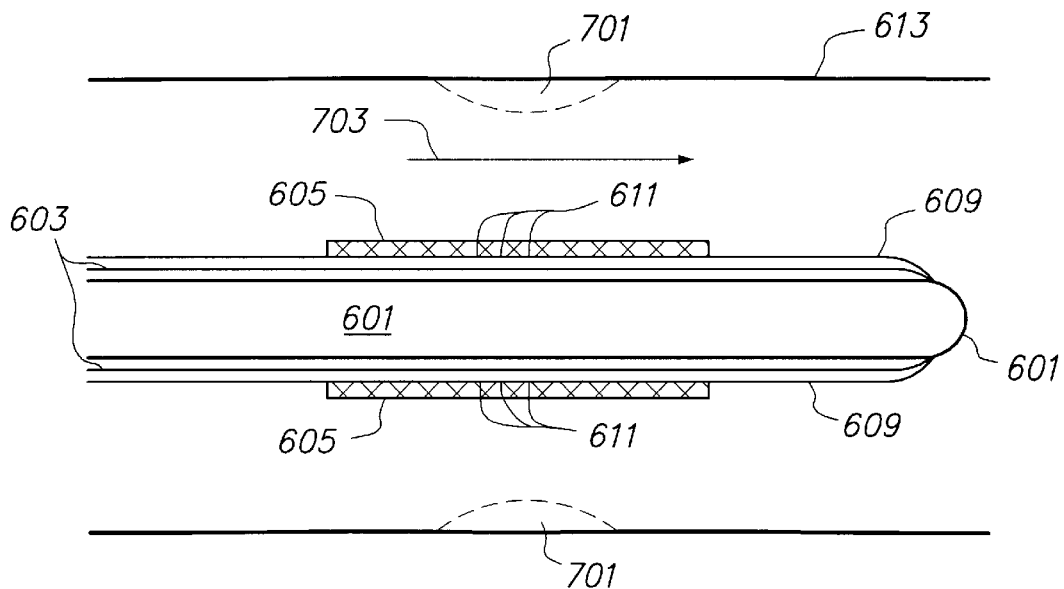
FIG. 6 is a schematic side view of a stent and balloon catheter which has been placed inside a diseased artery next to an area of stenosis. The stent is unexpanded and the inner balloon is deflated.

FIG. 6 depicts a schematic side view of a stent and balloon catheter which has been placed inside a diseased artery next to an area of stenosis (701). The stent and balloon catheter comprises a catheter body (601) fitted with uninflated non-porous inner balloon (603), outer balloon (609), which outer balloon has porous region (611), and unexpanded stent (605) encircling the catheter, the outer balloon and the inner balloon. Microcatheter techniques are used to insert the stent and balloon catheter into a diseased blood vessel (613) at the site of the desired vascular reconstruction, near the area of vascular stenosis (701).

Figure 7:
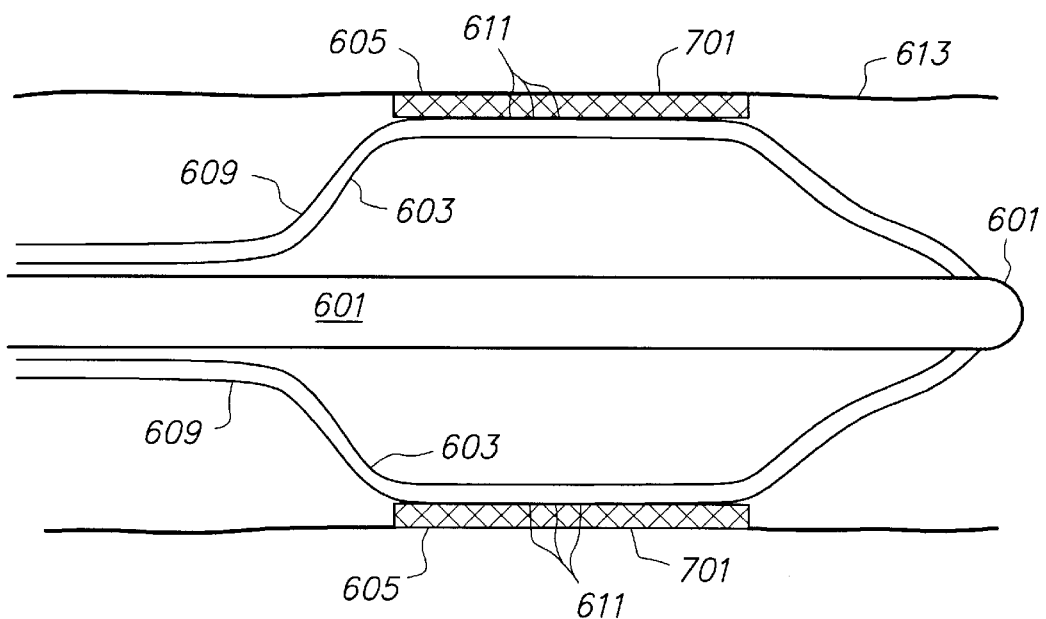
FIG. 7 is a schematic side view of a stent and balloon catheter which has been placed inside a diseased artery next to an area of stenosis. The inner balloon has been inflated, expanding the stent against the vascular wall in the area of the stenosis.

Then, as shown in FIG. 7, the non-porous inner balloon (603) is inflated. The inflated inner balloon pushes out against the vascular walls of diseased blood vessel (613), and expands stent (605) against the area of stenosis (701). Upon inflation of the inner balloon (603) and expansion of the stent (605), the area of stenosis (701) will be pushed back against the arterial walls.

Figure 8:
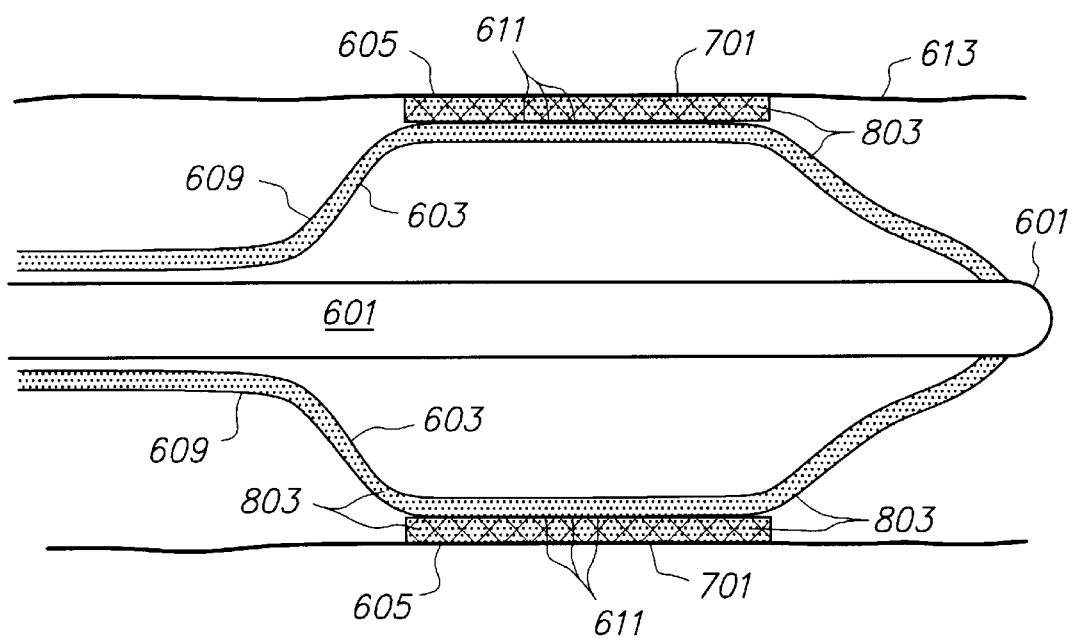
FIG. 8 is a schematic side view of a stent and balloon catheter which has been placed inside a diseased artery next to an area of stenosis. The inner balloon has been inflated, expanding the stent against the vascular wall in the area of the stenosis. Fluidic composition has been injected into the outer balloon and is permeating the porous region of the outer balloon so that it coats the walls of the stent and the vascular walls at the area of stenosis.

Then, as depicted in FIG. 8, fluidic composition (803) is delivered to the outer balloon (609). Fluidic composition (803) permeates the porous region (611) of the outer balloon and coats the stent and the walls of the diseased blood vessel at the area of stenosis (701). The pressure of the balloon against the layer of fluidic composition conforms the fluidic composition to the contours of the vascular wall and the mesh stent. The inner balloon can then be deflated and the catheter and balloons removed, leaving the expanded stent at the vascular site.

The fluidic composition then solidifies into a solid polymeric film, isolating the diseased portion of the artery, including the stenoic area, from the systemic blood flow.

After this vascular reconstruction, systemic blood flow will pass through the inside of the coated stent. The vascular reconstruction will prevent further growth of the diseased portions of the artery and provide for endothelialization of healthy arterial cells over the coated stent.

Alternatively, the vascular reconstruction demonstrated in this example could have been performed by use of a stent and then, to deliver the fluidic composition to the vascular site, a porous balloon catheter; or by use of a stent, a catheter to deliver the fluidic composition to vascular site, and a non-porous balloon catheter to conform the fluidic composition to the contours of the vascular site.

Example 7

Vascular Reconstruction and Remodeling of Vascular Blood Flow

The purpose of this example is to demonstrate procedures which can be used to treat diseased, non-aneurysmal arteries with vascular reconstruction. In this example, vascular reconstruction is used to reconstruct the vascular blood flow path away from undesired blood flow patterns.

Figure 9:
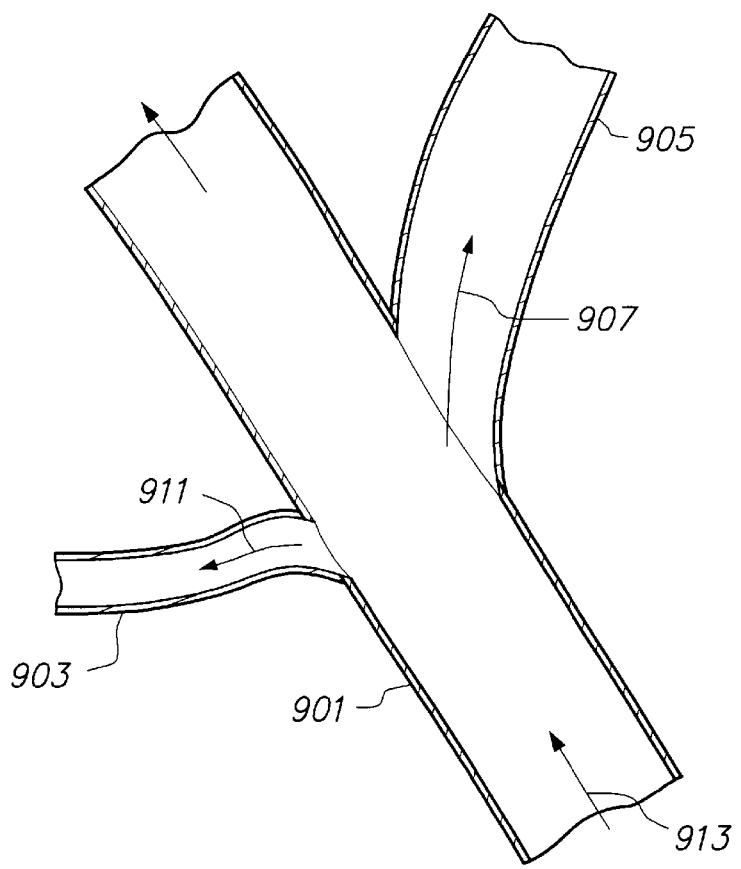
FIG. 9 is a schematic side view of a diseased artery with undesired blood flows.
Figure 10:
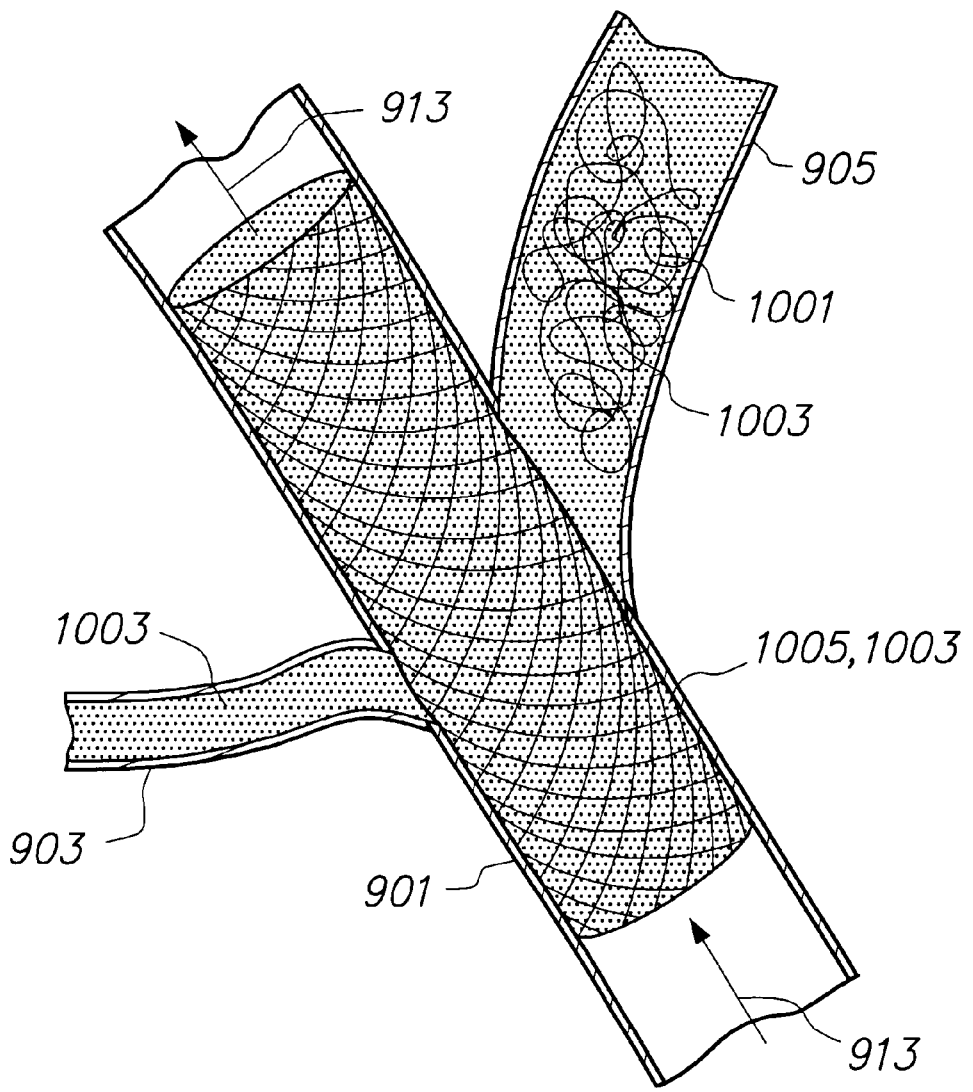
FIG. 10 is a schematic side view of diseased artery where fluidic composition either alone or with coils has filled the passageways of undesired blood flow and the fluidic composition has coated the mesh stent, isolating the diseased portions of the artery from systemic blood flow.

As shown in FIG. 9, a diseased artery (901) with two undesired blood flow branches (903) and (905) has been identified for vascular reconstruction. Prior to vascular reconstruction, systemic blood flow (913) is passing through the diseased artery as well as the undesired branches. This results in undesired blood flow (911) flowing into undesired branch (903) and undesired blood flow (907) flowing into undesired branch (905). As shown in FIG. 10, microcatheter techniques are used to deliver a mesh stent (1005) to the diseased artery at the site of the desired vascular reconstruction. Such techniques can include, but are not limited to, (1) delivering a self-expanding stent to the vascular site, (2) delivering a stent and balloon catheter to the site and inflating the balloon to expand the stent, or (3) triggering stent expansion by sliding back a sheath to release the stent. The mesh stent serves as a framework for the new vascular blood flow which will exclude the undesired branches.

A microcatheter is then inserted into the diseased artery, through the middle of the cylindrical mesh stent (1005) and threaded out through one of the openings in the mesh stent into undesired branch (905). Microcatheter techniques are used to insert non-particulate agents such as coils (1001) in undesired branch (905). The same or a different catheter can be used to fill the undesired branches with fluidic composition (1003). With respect to undesired branch (905), the fluidic composition will help to anchor the coils (1001) in place.

Then, fluidic composition (1003) is coated over the walls of the diseased artery and the mesh stent. This coating can be accomplished with the use of a porous balloon catheter which is inserted in the diseased artery, inside the cylindrical portion of the mesh stent (1005). The permeable balloon is inflated at the selected site, and fluidic composition (1003) flows out of the balloon and coats the walls of the diseased artery and the stent. In addition, the pressure of the balloon against the layer of the fluidic composition conforms the fluidic composition to the contours of the vascular wall and the stent.

The fluidic composition then solidifies into a solid polymeric film, isolating the diseased portions of the artery from the systemic blood flow.

After this vascular reconstruction, systemic blood flow (913) will now pass through the inside of the coated stent, bypassing the undesired branches (903) and (905). The vascular reconstruction will prevent further growth of the diseased portions of the artery and provide for endothelialization of healthy arterial cells over the coated stent.

Alternatively, the vascular reconstruction demonstrated in this example could have been performed by use of a stent and balloon catheter or by use of a stent, a catheter to deliver the fluidic composition to vascular site, and a non-porous balloon catheter to conform the fluidic composition to the contours of the vascular site.

What is claimed is:

1. A method for treating a diseased, non-aneurysmal artery in a mammalian patient which method comprises:
    (a) identifying the vascular site of a diseased, non-aneurysmal artery in a mammalian patient wherein said vascular site participates in the systemic blood flow of said patient;
    (b) inserting a stent into the diseased artery at the vascular site; and
    (c) delivering a fluidic composition to the vascular site which composition in situ forms a solid in and around the stent thereby isolating the vascular walls at the vascular site from systemic blood flow while retaining blood flow through the artery.

2. The method of claim 1 wherein the stent is an open or mesh stent.

3. The method of claim 1, which further comprises conforming the fluidic composition to the contours of the vascular site.

4. The method according to claim 1 which further comprises employing non-particulate agents to fill in the spaces in and around the stent.

5. The method according to claim 1 wherein the fluidic composition comprises a biocompatible polymer, a biocompatible contrast agent, and a biocompatible solvent which solubilizes the biocompatible polymer wherein sufficient amounts of the polymer are employed in the composition such that, upon delivery to the vascular site of the diseased artery, a polymer precipitate forms which coats the vascular wall of the diseased artery and the stent with a solid polymeric film thereby isolating the diseased portions of the artery from the systemic blood flow.

6. The method according to claim 1 wherein the fluidic composition comprises a biocompatible prepolymer, a contrast agent and optionally a biocompatible solvent.

7. A method for treating diseased, non-aneurysmal arteries by vascular reconstruction which method comprises:
    (a) endovascularly delivering to a vascular site a stent and balloon catheter, said stent and balloon catheter comprising a catheter fitted with an inner, non-porous balloon, an outer, porous balloon, and an unexpanded stent encircling the catheter, the outer balloon and the inner balloon;
    (c) inflating said inner balloon to expand the stent out to the vascular walls at said vascular site;
    (d) delivering to the vascular site, through the porous outer balloon, a fluidic composition which composition in situ forms a solid in and around the stent thereby isolating the vascular walls at the vascular site from systemic blood flow; the pressure of the balloon against the fluidic composition conforming said composition to the contours of the vascular site.

8. The method according to claim 7 wherein the fluidic composition comprises a biocompatible polymer, a biocompatible contrast agent, and a biocompatible solvent which solubilizes the biocompatible polymer wherein sufficient amounts of the polymer are employed in the composition such that, upon delivery to the vascular site of the diseased artery, a polymer precipitate forms which coats the vascular wall of the diseased artery and the stent with a solid polymeric film thereby isolating the diseased portions of the artery from the systemic blood flow.

9. The method according to claim 7 wherein the fluidic composition comprises a biocompatible prepolymer, a contrast agent and optionally a biocompatible solvent.

* * * * *